United States Patent [19]

Hino et al.

[11] 4,221,695

[45] Sep. 9, 1980

[54] ADSORBENT FOR ARTIFICIAL ORGANS

[75] Inventors: Kuniaki Hino, Tokyo; Yasuo Uehara, Iruma; Yasushi Nishimura, Tokyo; Kazuhiro Watanabe, Ichihara; Yoshio Okada, Tokyo, all of Japan

[73] Assignee: Kureha Kagaku Kogyo Kabushiki Kaisha, Tokyo, Japan

[21] Appl. No.: 6,493

[22] Filed: Jan. 25, 1979

[30] Foreign Application Priority Data

Feb. 6, 1978 [JP] Japan ................................. 53/12140

[51] Int. Cl.$^2$ ............................................. C08K 9/00
[52] U.S. Cl. ............................. 260/42.14; 106/308 M; 106/308 P; 106/308 C; 252/421; 252/428; 252/444; 260/42.25; 260/42.52; 521/101; 521/102; 521/109
[58] Field of Search ...................... 252/421, 428, 444; 260/42.14, 42.25, 42.52; 106/308 M, 308 P, 308 C; 521/101, 102, 109

[56] References Cited

U.S. PATENT DOCUMENTS

| | | | |
|---|---|---|---|
| 3,917,806 | 11/1975 | Amagi et al. | 252/444 |
| 3,953,345 | 4/1976 | Saito et al. | 252/444 |
| 4,045,368 | 8/1977 | Katori et al. | 252/444 |

FOREIGN PATENT DOCUMENTS

| | | |
|---|---|---|
| 51-148291 | 12/1976 | Japan . |
| 51-151693 | 12/1976 | Japan . |
| 1318324 | 5/1973 | United Kingdom . |
| 1383085 | 2/1975 | United Kingdom . |
| 1468982 | 3/1977 | United Kingdom . |
| 1474599 | 5/1977 | United Kingdom . |

*Primary Examiner*—Melvyn I. Marquis
*Attorney, Agent, or Firm*—Stevens, Davis, Miller & Mosher

[57] ABSTRACT

An absorbant for use in artificial organs which is obtained by mixing and dissolving pitch with an aromatic compound and a polymer or copolymer of a chain hydrocarbon, dispersing the resultant mixture in water giving rise to beads and subjecting these beads to a series of treatments of removing of the aromatic hydrocarbon, infusibilizing, carbonizing and activating.

9 Claims, 1 Drawing Figure

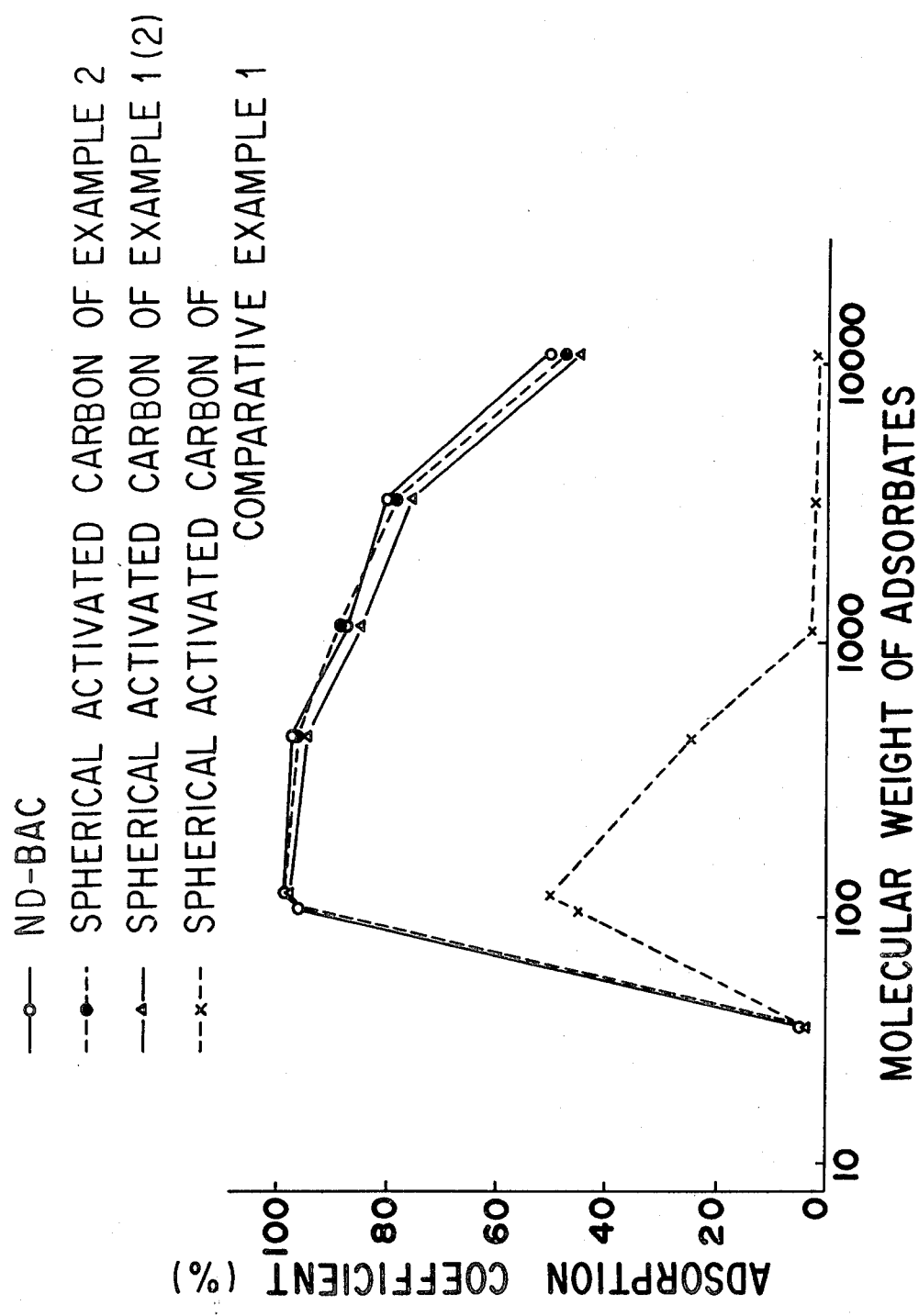

ADSORBENT FOR ARTIFICIAL ORGANS

This invention relates to adsorbents of the class to be used in artificial organs such as artificial kidneys, artificial livers, etc. More particularly, this invention relates to an adsorbent for use in artificial organs, which adsorbent is obtained by mixing and dissolving pitch with an aromatic compound as a solvent compatible with the pitch and a chain polymer of a hydrocarbon or a copolymer formed preponderantly of the hydrocarbon or a mixture of the polymer and copolymer, dispersing the resultant mixture in water thereby giving rise to beads of the pitch mixture, removing the solvent from the beads, infusibilizing them and activating through carbonizing to afford novel beads of activated carbon, washing the beads with water to produce dustfree beads of activated carbon (hereinafter called ND-BAC) and further subjecting the beads to an adsorption treatment with a substance possessed of bio-compatibility or directly coating the beads with a film-forming substance possessed of bio-compatibility.

Patients who have lost their renal functions or hepatic functions suffer from various physiological disorders caused by the accumulation of toxins within their living systems owing to the failure of the organs to function normally. The number of these patients is increasing year after year. In the circumstances, therefore, profound significance is to be attached to the task of development of substitutive devices capable of fulfilling the functions of the lost organs and excreting such toxins out of the living system.

Among the artificial kidneys which have theretofore been suggested, those of the principle that the removal of toxins is effected through dialysis of affected blood have found the most widespread acceptance. These artificial kidneys of the blood-dialysis type, however, have a disadvantage in that the dialysis of blood consumes much time and the equipment takes up much space. Thus, they are not necessarily quite satisfactory for the patients. In recent years, researches are promoted for the development of artificial kidneys of the adsorption type, with a view to eliminating the disadvantage.

As one modified version of the artifical kidney, an auxiliary liver system designed to fulfil partly the detoxifying function of the liver is now under development. As regards the adsorbents for use in the artifical organs of the adsorption type, beads of activated carbon are drawing increasing attention as possessing properties excelling those of the conventional crushed or pelletized activated carbons. For example, Japanese Patent Laid-Open Publication No. 148291/1976 discloses beads of activated carbon which are obtained by molding a pitch of crude oil origin in the form of beads, washing the beads repeatedly by various methods and thereby removing what would otherwise give rise to carbon dust as thoroughly as possible from the beads and thereafter causing fine carbon dust adhering to the surface of activated carbon to be immobilized with pyroxylin, etc. onto the activated carbon surface. Besides, Japanese Patent Laid-open Publication No. 151693/1976 discloses beads of activated carbon which are coated with a film-forming substance such as, for example, pyroxylin, polypropylene or vinyl chloride-vinylidene chloride copolymer with a view to enhancing the tenacity of beads and overcoming difficulties arising from free carbon dust and ignition ashes and which, immediately prior to their actual use in the purification of blood, are further coated with albumin etc. for the purpose of preventing the bead surface from causing adhesion and coagulation of blood components.

Examples of the application to clinical experiments of such coated activated carbon uses as the adsorbent in artificial organs are found in literature including the reports by Chang T.M.S. et al (Trans. A.S.A.I.O., 19, 314, 1973) (Trans. A.S.A.I.O., 16, 141-149, 1970), Odaka et al (Jinko Zoki [artificial organs], Vol. 5 No. 3, pp 171-176, 1976) and Mito et al (Jinko Zoki, Vol. 6 No. 3, pp 110-118, 1977). The clinical experiments have actually been performed on patients at various research organs and hospitals in foreign countries as well as in Japan. Substantially all the adsorbents used for this purpose are beads of activated carbon of petroleum oil origin.

Unfortunately, as is evident from the prior publications mentioned above, the conventional beads of activated carbon of petroleum oil origin are not perfectly free from the carbon dust which steals its way into the materials in the course of the preparation of activated carbon and from the carbon dust which forms as when molded beads are subjected to washing and other treatments. When such beads of activated carbon are to be used as the adsorbent in artificial organs through which the blood is directly infused, it is an indispensable requirement that the beads should be coated with a film-forming substance so as to preclude otherwise possible liberation of carbon dust from the bead surface and prevent blood components from being adhered on the bead surface.

Incidentally, the application of a film-forming substance to the surface of the adsorbent is nothing to be desired, because the applied substance goes to reduce the adsorption velocity of the matters to be adsorbed on the adsorbent and limit the molecular size of such matters being adsorbed. In the development of adsorbents for artificial organs from activated carbon products obtained by the conventional methods, therefore, efforts are taken in search of a film-forming substance or a method of coating which provides effective prevention of the liberation of carbon dust without entailing any reduction of the capacity of adsorbent.

For example, researches are now under way on the double coating involving the use of different film-forming substances, the multi-layer coating by use of one and the same film-forming substance and the voluminous coating by use of one and the same film-forming substance.

In the activated carbon products obtained by the coating methods mentioned above, the coats formed of the film-forming substance must be given a sufficiently ample thicknesses to ensure perfect preclusion of the liberation of carbon dust, even to the extent of reducing the adsorption property of the adsorbents particularly with respect to substances to be adsorbed possessed of relatively high molecular weights.

The inventors made a study with a view to eliminating the aforementioned various disadvantages suffered by the conventional techniques and succeeded in developing beads of activated carbon which entail very little liberation of carbon dust and enjoy high strength. They have, consequently, acquired a knowledge that these beads of activated carbon, when further treated with a bio-compatible substance, give rise to an adsorption suitable for use in artificial organs which liberates no carbon dust, exhibits an excellent adsorption property with respect to substances of medium to high molecular weights and possesses bio-compatibility. The present invention has issued from this knowledge.

Now, the present invention will be described in detail with reference to the drawing in which the relationship of molecular weight and adsorption as obtained with various beads of activated carbon is shown. The aforementioned beads of activated carbon which entail very little liberation of carbon dust and the method for the manufacture thereof are disclosed in the specification of the co-pending Japanese Patent Application No. 53-12139 filed under the even date in Japan by the same applicants of the present patent application. This activated carbon is obtained by following the known procedure disclosed by Japanese Patent Publication No. 18879/1975, except that the pitch used as the raw material is mixed in advance with a chain high polymer of a hydrocarbon, a copolymer formed preponderantly of said hydrocarbon or a mixture thereof. The beads of the activated carbon are produced by mixing a pitch having a softening point in the range of from 50° to 350° C. with at least one compatible aromatic compound as a solvent therefor and, at the same time that they are melted and blended with each other at a temperatures in the range of from 150° to 250° C., admixing therewith a chain high polymer of a hydrocarbon having a low decomposing property and molecular weight less than about 500,000 for good miscibility with the mixing system in the blending and liquefying temperature range mentioned above (for example, polyethylene such as "SUMIKATHENE G-806" of Sumitomo Chemical Co., Ltd., polypropylene such as "Moplen Type AS" of Montecatini Co., Ltd., polybutadiene such as "Nipol BR 1220" of Nippon Zeon Co., Ltd., or polystyrene such as "Esbrite GP-8" of Sumitomo Chemical Co., Ltd.) or a copolymer formed preponderantly of the hydrocarbon mentioned above (such as, for example, ethylene-vinylacetate copolymer such as "EVA FLEX-250" of Mitsui Polychemical Co., Ltd.) or a mixture of the polymer and the copolymer in an amount of from 0.1 to 10%, and more preferably, 0.5–8% by weight based on the weight of the pitch, then pouring the resultant molten pitch blend into water containing a suspending agent and kept at a temperature in the range of from 50° to 200° C., if necessary in an autoclave, and thereby dispersing the blend in the form of fine spherical particles (beads) and giving rise to beads of pitch, and thereafter subjecting the beads to the treatments for removing the aromatic compound used as the organic solvent in the molding process by extraction with a solvent which exhibits sparing solubility for the pitch and polymeric material but shows good miscibility with the added organic solvent, and infusibilization, carbonizing, activation and detergence by an ordinary method. The aforementioned aromatic compounds include aromatic hydrocarbons of one to three rings such as, for example, benzene, toluene, xylene, naphthelene, methyl naphthalene, dimethyl naphthalene, anthrancene, phenanthrene, triphenylene, diphenyl, diphenylmethane and diphenyl ether. The alkyl derivatives of these aromatic hydrocarbons may also be used. To the pitch, at least one of the aforementioned aromatic compounds is added. Although the amount in which the aromatic compound is added to the pitch is not particularly critical, the compound is desired to be added in an amount in the range of from 5 to 50 parts by weight based on 100 parts by weight of the pitch.

Usually, the infusibilization treatment is conducted in air while gradually heating from room temperature, and is completed at a temperature of below 400° C. The infusibilized spherical pitch is then heated and carbonized in an atmosphere of $N_2$ or steam, and activated at 900°–1000° C. As a result, there can be obtained highly spherical, very low dusting activated carbon of high strength.

The pitch used as the one component of the starting material is, preferably, that which has a softening point of 50°–350° C., more preferably 150°–250° C., a carbon content of 80–97% by weight, a hydrogen/carbon atomic ratio of 0.3–2.0, and a nitrobenzene-insoluble matter content below 60% by weight. The term "softening point" used herein is intended to mean the temperature at which a piston of a KŌKA type flow tester charged with 1 g of the specimen comes to a first stop during its lowering movement which occurs upon heating the specimen at a temperature increasing at a rate of 6° C./min. under a load of 10 kg/cm$^2$. The term "nitrobenzene-insoluble matter content" means a ratio by % by weight of insoluble matter remaining when 1 g of pitch powder is added to 100 ml of nitrobenzene and dissolved at 40° C.

Usually, any pitches derived from petroleum cracking or derived from coal are adequately used.

The beads of activated carbon thus produced are true spheres whose physical properties are 0.1 to 1.5 mm in particle diameter, 0.5 to 1.5 g/ml in particle density, 800 to 1600 m$^2$/g in specific surface area, not less than 0.3 ml/g in volume of pores as measured in the range of less than 100 Å in pore-radius and less than 0.5 ml/g in volume of pores as measured in the range of 100 to 100,000 Å in pore-radius. The ash content of the activated carbon is less than 0.5% by weight.

The beads of activated carbon obtained by the method described above enjoy the great freedom from carbon dust formation which has never been attained in the beads of activated carbon obtained by the conventional methods. Thus, they can be advantageously used as the adsorbent in artifical organs. Owing to the high freedom from carbon dust formation which features the beads of activated carbon provided by this invention, the beads can be used advantageously as the adsorbent for artificial organs without entailing a troublesome treatment otherwise required to be given to the activated carbon for removal of carbon dust.

By simply causing the beads of activated carbon (ND-BAC) to adsorb thereon a bio-compatibile substance or coating the surface of the beads with a bio-compatible substance (film-forming substance) there can be provided an adsorbent for artificial organs which has no possibility of carbon dust formation and exhibits a notably high adsorption property with respect to substances possessing molecular weights greater than about 3000.

The adsorption of the bio-compatible substance by the beads of activated carbon (ND-BAC) is accomplished by immersing the beads of activated carbon in the aqueous solution of a biological component (blood component) such as albumin or heparin, removing the wet beads from the solution and drying them. When the beads of activated carbon on which the biological component has been deposited as described above are used as the adsorbent in an artificial organ and the blood is caused to flow through the adsorbent, the blood and the biological component deposited on the adsorbent are held in an equilibrated state in the vicinity of the surface of the beads of activated carbon and the activated carbon consequently behaves as if it were a part of the vital system. Thus, the adsorbent provides excellent biocompatibility.

The coating of the surface of the beads of activated carbon (ND-BAC) with a bio-compatibile substance is accomplished by causing a bio-compatible film-forming substance such as, for example, albumin, gelatin, pyroxylin, cellulose acetate or polyhydroxyethyl methacrylate (which may be subjected in advance to a treatment for crosslinking if necessary) to be uniformly applied to the surface of the beads of activated carbon by use of the phase separation method, the immersion method or some other suitable treatment. The beads of activated carbon (ND-BAC) which are used for the purpose of this invention enjoy an ideal surface coating condition for the coating with a film-forming substance in addition to the aforementioned high freedom from carbon dust formation. In the coating treatment, therefore, the beads of activated carbon have an advantage that, by a simple treatment, they can be uniformly coated with a thin film without requiring use of as large an amount of film-forming substance as heretofore required. The coating thus effected enhances the strength of the individual beads of activated carbon without imparing the adsorption property of the beads with respect to substances possessing medium to high molecular weights. The application of the bio-compatibility substance to the ND-BAC is effected more advantageously by the adsorption than by the coating, because the former method brings about virtually no reduction of the adsorption property of the ND-BAC itself as compared with the latter method.

As described above, the adsorbent of the present invention is produced by simply causing the newly developed beads of activated carbon (ND-BAC) to adsorb a bio-compatible substance directly thereon or to be coated to a slight extent with the substance. Thus, the adsorbent of the present invention fully exhibits the adsorption property which is inherent to the beads of activated carbon and, at the same time, serves its purpose fully in artificial organs owing to its bio-compatibility.

Moreover, since the adsorbent of this invention is usable in artificial organs designed to be operated under very severe physiological conditions, it is naturally expected to find utility additionally in the medical field and foodstuff industry which necessitate the adsorption treatment.

This invention will be described more specifically with reference to working examples herein below.

EXAMPLE 1

(1) In an autoclave having an inner volume of 1 liter, 300 g of pitch obtained by the cracking of petroleum oil was mixed with 100 g of naphthalene and 2% by weight based on the pitch of polyethylene ("SUMIKATHENE G-806": Sumitomo Chemical Co., Ltd. ) under continued agitation at 180° C. for two hours for homogeneous dissolution. The resultant pitch mixture was poured into water containing therein 0.5% by weight of polyvinyl alcohol and heated in advance to 160° C., and dispersed therein by agitation at a rate of 1200 rpm for 20 minutes so that the pitch is converted into small spherical particles. Then the water containing the dispersed pitch mixture was wholly cooled to give solidified beads of pitch. The beads were dehydrated, extracted with n-hexane to remove naphthalene therefrom, subsequently transferred into a fluidized bed formed by a forced flow of air, heated from room temperature to 300° C. at a temperature increasing rate of 30° C./hour to afford infusibilized beads of pitch. Subsequently, the beads were carbonized by being heated in steam to 900° C., then kept at 900° C. and then washed with water to produce beads of activated carbon (ND-BAC).

(2) In 500 ml of distilled water, 100 g of the beads of activated carbon obtained in (1) were dispersed. Then in an ultrasonic wave washer (Model NS-50, made by Nihon Seiki), the dispersed beads were washed by means of ultrasonic waves for about 30 minutes and thereafter placed on a stainless steel gauze and rinsed with running water. This ND-BAC was dispersed in 200 ml of an ethanol-water (80:20) mixture containing 0.1% by weight of polyhydroxyethyl methacrylate. Then to the dispersion, 600 ml of distilled water was gently added to have polyhydroxyethyl methacrylate isolated as an independent phase to effect the first coating of the ND-BAC with polyhydroxyethyl methacrylate. The coated beads were transferred onto a stainless steel gauze, washed with distilled water to remove the excess coating material from the beads, and dried to give dustfree beads of activated carbon coated with polyhydroxyethyl methacrylate.

EXAMPLE 2

In 500 ml of distilled water, 100 g of the beads of activated carbon obtained in Example 1 (1) were dispersed. Then, the dispersed beads were washed by means of ultrasonic waves for about 30 minutes in the same ultrasonic wave washer as used in Example 1 (2). They were placed on a stainless steel gauze and washed with running water.

This ND-BAC was immersed in an aqueous 1% albumin solution for about two hours to have albumin adsorbed by the ND-BAC. The beads were separated by decanting the aqueous albumin solution and then dried to afford albumin-treated beads of activated carbon.

Comparitive Example 1

To 500 ml of distilled water, 100 g of conventional beads of activated carbon (produced by the method described in Japanese Patent Publications No. 18879/1975 and No. 76/1967) were added. The beads in the water were washed in an ultrasonic wave washer for 30 minutes. Then, the beads were separated from the washing. They were again placed in 500 ml of fresh distilled water and subjected to the same procedure of washing as in the first washing. The third washing was similarly given to the beads. After removal of the third washing, the cleaned conventional beads of activated carbon was washed with running water. The beads thus cleaned were not yet competely free from carbon dust.

Subsequently, the cleaned conventional beads of activated carbon were dispersed in 200 ml of an ethanol-water (80:20) mixture containing 0.2% by weight of polyhydroxyethyl methacrylate. To the dispersion, 600 ml of distilled water was added to effect phase separation. The beads were then transferred onto a stainless steel gauze to be dehydrated and then dried. The dried beads of activated carbon are again dispersed in 200 ml of an ethanol-water (80:20) mixture containing 1% by weight of polyhydroxyethyl methacrylate. To the dispersion, 600 ml of distilled water was added to effect phase separation. The beads were thereafter dehydrated on a stainless steel gauze and dried.

Comparative Example 2:

In 200 ml of distilled water, 100 g of conventional beads of activated carbon (same as those of Comparative Example 1) were dispersed. The beads in the water were washed with an ultrasonic wave washer for 30 minutes. Then, the beads were separated from the washing. The washing of the beads with 500 ml of distilled water was carried out a total of three times. After removal of the third washing, the beads are transferred onto a stainless steel gauze and washed with running distilled water.

Subsequently, the cleaned beads of activated carbon were dispersed in 200 ml of an ethanol-water (80:20) mixture containing 0.2% of polyhydroxyethyl methacrylate. To the dispersion 600 ml of distilled water was added to effect phase separation. Then, the beads were transferred onto a stainless steel gauze, there to be dehydrated and dried. The beads were dispersed again in 200 ml of an ethanol-water (80:20) mixture containing 1% by weight of polyhydroxyethyl methacrylate, followed by addition of 600 ml of distilled water for phase separation. The beads were then transferred onto a stainless steel gauze, there to be dehydrated and dried. For further removal of carbon dust, the beads of activated carbon were subjected to a similar coating treatment using an ethanol-water mixed medium (80:20) containing 3% by weight of polyhydroxyethyl methacrylate, to afford dustfree beads of activated carbon.

The results of the performance test conducted on the beads of activated carbon obtained as described in Examples 1 and 2 and Comparative Examples 1 and 2 are shown in Table 3

Test 1:

A 10-g sample was weighed out each from the beads of activated carbon obtained by washing or surface treatment in Examples 1 and 2 and Comparative Examples 1 and 2. The sample was placed in a 200-ml Erlenmeyer flask in conjunction with 150 ml of distilled water filtered in advance through a 0.45-$\mu$ membrane filter and shaken at 130 rpm for 60 minutes with a mini-shaker (Model SS-80, made by Tokyo Rikakiki). Then, 100 ml of the liquid obtained in the flask was passed through a 0.3-$\mu$ membrane filter to collect free carbon dust from the liquid. The carbon dust collected on the filter is shown in the accompanying photograph. A count was taken of those particles of free carbon dust in the dispersion having diameters exceeding 1.2 $\mu$. The results are shown in Table 1.

The photographs show the conditions of carbon dusts which have been liberated from the different beads of activated carbon and collected on the membrane filters. Photograph A1 represents the residue of the washing from the cleaned ND-BAC and Photograph A2 represents the residue of the washing from the first treatment of ND-BAC with an ethanol-water mixed medium (80:20) containing 0.1% by weight of polyhydroxyethyl methacrylate. Photograph A3 represents the residue of the washing from the treatment of ND-BAC with an aqueous 1% by weight albumin solution. Photograph B1 represents the residue of the washing from the cleaning of conventional beads of activated carbon. Photograph B2 represents the residue of the washing from the first treatment of conventional beads of activated carbon with an ethanol-water mixed medium (80:20) containing 0.2% by weight of P-HEMA. Photograph B3 represents the residue of the washing from the second treatment of conventional beads of activated carbon with an ethanol-water mixed medium (80:20) containing 1% by weight of P-HEMA. following the first treatment with an ethanol-water mixed medium (80:20) containing 0.2% by weight of P-HEMA. Photograph B4 represents the residue of the washing from the third treatment of conventional beads of activated carbon with an ethanol-water mixed medium (80:20) containing 3% of P-HEMA following the first treatment with an ethanol-water mixed medium (80:20) containing 0.2% by weight of P-HEMA and the second treatment with an ethanol-water mixed medium (80:20) containing 1% by weight of P-HEMA.

Table 1

|  | Number of free carbon dust particles (pieces/ml) |
|---|---|
| Coated beads of activated carbon of Example 1 | Substantially no particle |
| Coated beads of activated carbon of Example 2 | Substantially no particle |
| Coated conventional beads of activated carbon of Comparative Example 1 | 100 to 300 |
| Coated conventional beads of activated carbon of Comparative Example 2 | 0 to 20 |

Test 2

Samples each weighing 2.0 g were taken from the ND-BAC obtained by the washing of beads of activated carbon in Step (1) of Example 1, and from the beads of activated carbon obtained by the treatments of adsorption or coating in Example 1 (2), Example 2, Comparative Example 1 and Comparative Example 2. These samples were placed separately in 200-ml phosphate buffer solutions of various substances of different molecular weights (urea, uric acid, creatinine, Red-102, vitamine $B_{12}$, inulin and cytochrome) (5 to 20 mg/dl), shaken for three hours to effect adsorption, and removed from the solutions. The residual solutions were analyzed to determine the concentrations of the substances adsorbed by the beads and consequently the adsorption coefficients on the basis of the following formula.

Coefficient of adsorption=[{(concentration before adsorption)−(concentration after adsorption)}/(concentration before adsorption)]×100 (%)

The results are shown in the accompanying drawing. It is clearly seen from the drawing:

(1) That virtually no difference exists between the adsorption property of ND-BAC and that of the beads activated carbon obtained in Example 2.

(2) That, in the ND-BAC which has absolutely no possibility of dust liberation, the treatment of coating carried out by the procedure of Example 2 causes only a little reduction in the adsorption property of the beads.

(3) That conventional beads of activated carbon have their adsorption property notably reduced when they were coated to an extent enough for perfect preclusion of dust liberation.

The ND-BAC, when used as the adsorbent in artificial organs, exhibits a notably improved adsorption property as compared to the conventional beads of activated carbon. The effect of the adsorption is particularly conspicuous with respect to substances having medium or higher molecular weights.

Test 3:

Samples each weighing 5 g were taken from the surface-treated beads of activated carbon obtained in Examples 1 and 2 and Comparative Example 1. Each sample was placed in a glass column. Then, 50 ml of rabbit's blood containing 5 units of heparin per ml was passed through the packed sample at a rate of 20 ml/min for 30 minutes. Then, the circulation of the blood through the column was stopped and the blood was removed from the column. The sample was washed with 200 ml of physiological saline solution and dried in a current of nitrogen gas. The dried beads of activated carbon were examined to determine the adhesion of blood platelets and blood corpuscles. The results are shown in Table 2.

Table 2

|  | Adhesion of blood platelets | Adhesion of blood corpuscles |
| --- | --- | --- |
| Beads of activated carbon of Example 1 (2) | — | — |
| Beads of activated carbon of Example 2 | — | — |
| Beads of activated carbon of Comparative Example 1 | + | + |

Note:
(—: No adhesion, +: adhesion)

Preparation Examples of Activated Carbons

Preparation of Starting Pitch:

Starting pitch A was that which was obtained by spraying crude oil Ceria into steam heated to 2000° C. to thermally crack in a contact time of 0.005 seconds, distilling the tar-like substance obtained after rapid cooling of the cracked oil, and collecting fractions of boiling points below 430° C. as calculated at a normal pressure. This pitch has a softening point of 201° C., a nitrobenzene-insoluble matter of 37%, a carbon content of 95%, and a hydrogen/carbon atomic ratio of 0.54.

Starting pitch B was that which was obtained by distilling a residual oil secondarily produced on ethylene cracking to remove fractions of boiling points below 540° C. from the oil, and which has a softening point of 225° C., a nitrobenzene-insoluble matter content of 21%, a carbon content of 94% and a hydrogen/carbon atomic ratio of 0.61. Production of Activated Carbon:

300 g of each of the thus obtained pitches, 100 g of naphthalene and each of polymeric materials indicated in Table 1 and used in an amount of 0 - 10% (by weight) of the pitch were placed in a 1-l autoclave, mixed, and molten or liquefied while agitating at 180° C. for 2 hours. The mixture was discharged into hot water heated to 160° C. and containing 0.5% by weight polyvinyl alcohol in an autoclave, and dispersed at 1200 r.p.m. for 20 minutes for conversion into spherical forms, followed by cooling the system to obtain pitch spheres. The water was removed and the naphthalene in the spheres was extracted with n-hexane. The spheres were then placed in fluidized bed, in which they were heated from room temperature up to 300° C. at a rate of 30° C./hr to give infusible pitch spheres. Thereafter, the spheres were heated to 900° C. for carbonizing in an atmoshpere of a gaseous mixture consisting of 50vol% of nitrogen, 47vol% of steam and 3vol% of oxygen and kept at 900° C. to obtain activated, spherical carbon.

Table 3

| | | Examples of Invention | | | | | | | | Comparative Examples | | Commercially available carbon A based on coal | Commercially available carbon B based on coconut husk |
|---|---|---|---|---|---|---|---|---|---|---|---|---|---|
| starting pitch | | A | A | A | A | A | A | B | B | A | B | | |
| added chain polymeric material* | | Polyethylene (P.E.) | Polyethylene (P.E.) | Polyethylene (P.E.) | Polybutadiene (P.B.) | Polystyrene (P.S.) | ethylene-vinylacetate copolymer (EVA) | Polyethylene (P.E.) | Polypropylene (P.P.) | | | | |
| amount of the chain polymer (% by weight of the pitch) | | 0.5 | 3.0 | 7.0 | 1.0 | 1.0 | 3.0 | 1.0 | 3.0 | 0 | 0 | — | — |
| Characteristic Properties of Activated Carbon | Iodine absorption mg/g | 960 | 1080 | 1020 | 960 | 1040 | 960 | 1100 | 1050 | 1080 | 1130 | 980 | 1100 |
| | caramel decoloration % | 70 | 83 | 88 | 72 | 89 | 82 | 93 | 79 | 82 | 91 | 92 | 80 |
| | bulk density g/ml | 0.57 | 0.55 | 0.52 | 0.57 | 0.52 | 0.58 | 0.51 | 0.57 | 0.59 | 0.56 | 0.45 | 0.48 |
| | specific surface area m²/g | 1000 | 1150 | 1060 | 1010 | 1050 | 1000 | 1100 | 1100 | 1150 | 1200 | 950 | 1150 |
| | dust test A wt % | no-detected | no-detected | no-detected | no-detected | no-detected | no-detected | no-detected | no detected | 0.18 | 0.10 | 4.7 | 2.5 |
| | dust test B % | 85 | 89 | 94 | 82 | 83 | 79 | 96 | 83 | 2 | 19 | *0 | *0 |
| | strength % | 98.0 | 99.0 | 98.6 | 98.2 | 97.6 | 96.4 | 99.2 | 98.6 | 95.2 | 94.9 | 84.1 | 85.6 |

(Note)
*
P.E.: "SUMIKATHENE G-806" (Sumitomo Chemical Co., Ltd.)
P.B.: "Nipol BR 1220" (Nippon Zeon Co., Ltd.)
P.S.: "Esbrite GP-8" (Sumitomo Chemical Co., Ltd.)
EVA: "EVA FLEX-250" (Mitsui Polychemical Co., Ltd.)
P.P.: "Moplen Type AS" (Montecatin Co., Ltd.)

(Note):
The characteristic properties of the activated carbon in the Table were determined as follows:
Measuring Methods
Iodine Adsorption: Determined according to the method prescribed in JIS K-1474.
Caramel Decoloration: Determined according to the method prescribed in JIS K-1412.
Surface Area: Determined according to the $N_2$ adsorption method.
Dust test A: 10 g of a sample and 50 ml of distilled water were placed in a glass container with a diameter of 60 mm and a height of 80 mm and shaked at an amplitude of 40 mm at 250 r.p.m. for 30 minutes. The resulting suspension was passed through a 100 mℓ screen for filtration and washed with fresh distilled water. The filtrate was evaporated to dryness, followed by measuring an amount of the resulting fine powder.
Dust test B: 5 g of activated carbon was placed in a 200 ml Erlenmeyer flask, to which 50 ml of distilled water was added. After degassing, the flask was sealingly stoppered and shaked in a manner similar to the case of the above method A. Immediately after the shaking, the supernatant liquid was sampled and subjected to a measurement of light transmittance by means of a spectrophotometer using a wavelength of 660 nm.
Strength: Determined according to the method of JIS K-1474.
*In the item "Dust test B", the both types of commercially available carbon were found to produce large amount of black carbon, and 0.5 g of each sample was used to conduct the measuring test but little or no passage of light was recognized.

Each of the activated carbons according to the present invention, which have been obtained in the "Preparation Examples of Activated Carbon" showed abourable test results nearly equal to those shown by the activated carbons obtained in Examples 1 and 2.

It will be appreciated by those skilled in the art that the instant specification and examples are set forth by way of illustration and not limitation, and that various changes and modifications may be made without departing from the spirit and scope of the present invention, which is to be limited only by the scope of the appended claims.

What is claimed is:

1. In an adsorbent for use in artificial organs including beads of activated carbon, the improvement which comprises: said beads of activated carbon being prepared by the steps of heating with continued stirring a mixture of a pitch having a softening point of 50° to 350° C., a carbon content of 80 to 97% by weight, an atomic ratio to hydrogen to carbon of 0.3 to 2.0 and a content of nitrobenzene-insoluble fraction below 60% by weight, an aromatic compound miscible with said pitch in an amount of 5 to 50 percent by weight of said pitch and a polymer and/or copolymer of chain hydrocarbon having said hydrocarbon moiety as a major component thereof, and thereby homogeneously liquifying said mixture, dispersing the thus liquified mixture in an aqueous solution containing a suspending agent and thereby obtaining beads of said mixture dispersed in said solution, and subjecting the thus obtained beads to a series of treatments of removing of said aromatic hydrocarbon, infusibilizing, carbonizing and activating.

2. The adsorbent according to claim 1 in which said step of heating of said mixture is carried out at a temperature of 150° to 200° C.

3. The adsorbent according to claim 1 in which said liquified mixture is dispersed in said aqueous solution at a temperature of 50° to 200° C.

4. The adsorbent according to claim 1 in which said polymer and/or copolymer of chain hydrocarbon has a molecular weight of less than about 500,000.

5. The adsorbent according to claim 1 in which the starting mixture contains 0.5 to 8% by weight of said polymer and/or copolymer of chain hydrocarbon based on the amount of said pitch.

6. The adsorbent according to claim 1 in which said polymer and/or copolymer of chain hydrocarbon is selected from the group consisting of polyethylene, polypropylene, polybutadiene, polystyrene, copolymer of ethylene and vinyl acetate and their derivatives.

7. The adsorbent according to claim 1 in which said aromatic compound is selected from the group consisting of benzene, toluene, xylene, naphthalene, triphenylene, diphenylmethane, diphenyl ether and their alkyl derivatives.

8. The adsorbent according to claim 1 in which said beads of activated carbon have the following physical characteristics: being spheres of 0.1 to 1.5 mm in diameter; having density of 0.5 to 1.5 g/ml; having a specific surface area of 800 to 1,600 $m^2/g$; having a micropore volume of above 0.3 ml/g as determined in the range of radius of micropore of below 100Å, and also of below 0.5 ml/g as determined in the range of radius of micropore of between 100 and 100,000 Å; and having an ash content of below 0.5% by weight.

9. The adsorbent according to claim 1 in which the surface of said beads adsorbed or is coated with a therapeutically effective amount of bio-compatible substance selected from the group consisting of albumin, gelatin, cellulose nitrate, cellulose acetate, poly(hydroxylethyl methacrylate) and their derivatives.

* * * * *

UNITED STATES PATENT AND TRADEMARK OFFICE
CERTIFICATE OF CORRECTION

PATENT NO. : 4,221,695
DATED : September 9, 1980
INVENTOR(S) : Kuniaki HINO ET AL It is certified that error appears in the above-identified patent and that said Letters Patent are hereby corrected as shown below:

Column 1, line 45, change "artifical" to --artificial--

Column 1, line 48, change "artifical" to --artificial--

Column 3, line 58, change "naphthelene" to --naphthalene--

Column 3, line 59, change "anthrancene" to --anthracene--

Claim 1, line 28, change "liquifying" to --liquefying--

Claim 1, line 29, change "liquified" to --liquefied--

Claim 3, line 2, change "liquified" to --liquefied--

Signed and Sealed this

Seventeenth Day of March 1981

[SEAL]

Attest:

RENE D. TEGTMEYER

Attesting Officer

Acting Commissioner of Patents and Trademarks